(12) United States Patent
Allart et al.

(10) Patent No.: US 8,246,972 B2
(45) Date of Patent: Aug. 21, 2012

(54) VETERINARY DERMATOLOGIC COMPOSITION

(75) Inventors: Jean-Claude Allart, Bruay Labuissiere (FR); Jean-Marie Lefevre, Amiens (FR); Jacques Peyrot, Clermont Ferrand (FR)

(73) Assignee: Dermaconcept JMC, Amiens (FR)

( * ) Notice: Subject to any disclaimer, the term of this patent is extended or adjusted under 35 U.S.C. 154(b) by 1047 days.

(21) Appl. No.: 10/470,299

(22) PCT Filed: Jan. 29, 2002

(86) PCT No.: PCT/EP02/01120
§ 371 (c)(1), (2), (4) Date: Sep. 30, 2004

(87) PCT Pub. No.: WO02/060406
PCT Pub. Date: Aug. 8, 2002

(65) Prior Publication Data
US 2005/0037035 A1    Feb. 17, 2005

(30) Foreign Application Priority Data
Jan. 29, 2001   (WO) .............. PCT/EP01/01019

(51) Int. Cl.
*A61K 7/075* (2006.01)
(52) U.S. Cl. .................................... 424/405; 424/70.23
(58) Field of Classification Search ............ 424/405
See application file for complete search history.

(56) References Cited

U.S. PATENT DOCUMENTS

| | | | | |
|---|---|---|---|---|
| 5,882,665 | A | * | 3/1999 | Meyers et al. ............. 424/401 |
| 6,306,383 | B1 | | 10/2001 | Crandall |
| 6,361,806 | B1 | * | 3/2002 | Allen ...................... 424/740 |

FOREIGN PATENT DOCUMENTS

| | | |
|---|---|---|
| DE | 196 02 108 A1 | 7/1997 |
| DE | 196 02 111 A1 | 7/1997 |
| FR | 2 747 307 A1 | 10/1997 |
| WO | 98/49999 A2 | 11/1998 |
| WO | 00/53568 A1 | 9/2000 |

OTHER PUBLICATIONS

Bibel et al (Topical sphingolipids in antisepsis and antifungal therapy. Clin Exp Dermatol. Sep. 1995;20(5):395-400).*
Noble et al (Pathogenesis and management of wound infections in domestic animals. Veterinary Dermatology. vol. 8 Issue 4, pp. 243-248 (1997).*
Bibel et al, "Topical sphingolipids in antisepsis and antifungal therapy"; *Chemical and Experimental Dermatology*, vol. 20, pp. 395-400, 1995.
Hamanaka, et al., Human Epidermal Glucosylceramides are Major Precursors of Stratum Corneum Ceramides, The Society for Investigative Dermatology, Inc., 2002, 416-425.

* cited by examiner

*Primary Examiner* — Jake M. Vu
(74) *Attorney, Agent, or Firm* — Merchant & Gould

(57) ABSTRACT

This invention relates to the use of an active compound selected from the group comprising a sphingoid base, a sphingoid base derivative or a mixture of two or more these compounds for manufacturing a cosmetic composition suitable for topical application with animals having an at least partly fur covered skin for maintaining and/or repairing the keratoseborrheaic condition of the skin and/or fur.

19 Claims, No Drawings

VETERINARY DERMATOLOGIC COMPOSITION

FIELD OF THE INVENTION

The present invention relates to a veterinary dermatologic composition according to the preamble of the first claim.

BACKGROUND OF THE INVENTION

The skin and/or fur of an animal form a barrier to the environment, this barrier being capable of adapting itself to varying environmental conditions. Besides this, the skin and/or fur play an important physiological role in providing physical protection, assisting in the thermal regulation of the organism and providing a metabolic, sensorial and storage function. The physical barrier function of the skin is mainly exerted by the outermost lipid layer or stratum corneum. The ceramides present in the stratum corneum ensure protective properties towards the environment and form a lipid filter limiting evaporation of moisture from and controlling permeation of external substances into the skin.

Besides this physical barrier function, the skin also exerts a chemical barrier function as its surface is colonised by a wide variety of microorganisms that assist in maintaining a natural equilibrium of the skin. However environmental action and contact of the skin with cleansing or other products may involve distortion of this natural equilibrium, an uncontrollable outgrowth of certain micro-organisms within the skin microflora and the consequential impaired lipid barrier function and dermatologic infections.

It has been found in the recent years that also with animals, in particular furry animals, domestic animals as well as farm animals, the number of cutaneous infections where overpopulations of microorganisms intervene is severely increasing. In particular, the occurrence of primitive infections, dermatoses over-infections and parasitoses has been more frequently observed. It is believed that the changing living conditions of the animals, the ensuing occurrence of bacterial and fungal overpopulation and a consequential weakening of the fur, may be possible causes thereof.

In this respect it has for example been observed with animals like cats and dogs that dermatoses and parasitoses induce severe scratching of the animal, which in turn involves alteration of the microbial microflora residing on the fur and skin, inflammatory reactions and keratinisation troubles. The latter are mostly treated through application of antibiotics and anti-inflammatory agents associated in an emollient. These products however have been found to be inconvenient because of their aggressiveness to the skin and fur and because they do not respect the ecoflora naturally occurring with the animal.

It becomes apparent that malfunctioning of the cutaneous barrier may involve widely varying immunologic reactions with the animal, in particular an augmentation of the microbial and fungal sensitivity, a bacterial proliferation and inflammatory reactions. In particular, with animals like cats and dogs, localised or general keratoseborrheaic phenomena resulting from problems associated with sebum secretion or keratinisation anomalies, constitute a characteristic reaction for furry animals.

The observed increase of the occurrence of primitive infections, dermatoses over-infections and parasitoses thus obviates the need to a composition, suitable for topical application on animal skin and/or fur, the composition being capable of treating these phenomena.

STATE OF THE ART

From WO 98/49999 it is known that sphingoid base containing formulations show growth-inhibitory activity against gram-negative as well as against gram-positive bacteria, when present in a concentration of at least 0.005 wt. %. Antimicrobial activity of sphingoid bases has been found against bacteria, yeasts and fungi. Typical applications include treatment of acne, dandruff, mycoses, i.e. cosmetic and/or dermatological applications on skin and hair.

Bibel et al in Clinical and Experimental Dermatology 1995, 20, 395-400 express their doubt about the suitability of sphingosin and sphinganin in clinical uses for their antimicrobial and anti-fungal activity. Formulations containing sphinganin were effective against *Candida albicans* and *Staphylococcus aureus*, in test experiments where inflammated, depilated guinea pig skin are used as simulators for human skin. Sphingosin had little effect. However, anti microbial activity against staphylococcus present on human tissue does not necessarily entail activity against specific staphylococci appearing with animals.

DE-A-196 02 108 and DE-A-196 02 111 relate to the use of sphingosin or phytosphingosin based sphingolipids as a deodorant. The object of using sphingosin or phytosphingosin is to obtain deodorant which is capable of selectively fighting those bacteria that are responsible for the unwanted sweat odour with human beings, leaving the normal microbial population and the human temperature regulating system unaffected.

WO95/03028 relates to a skin-renewal-stimulating cosmetic composition for frequent and repeated topical application to normal skin. The composition contains skin-renewal-stimulating acids for improving the appearance and condition of the skin. The long-term irritation induced by topical application these skin-renewal-stimulating acids is reduced through incorporation of a sphingosin material into the formulation.

The above-described applications are mainly limited to the field of cosmetic products, the use of sphingoid bases in veterinary applications not being touched.

SUMMARY OF THE INVENTION

It is the aim of the present invention to provide a cosmetic and pharmaceutical composition, for topical application on animal skin and/or fur, the composition being capable of regulating anomalies occurring with sebum secretion by the skin, regulating/maintaining the processes of desquamation and physiological keratinisation of the skin, regulating and treating primitive infections, dermatoses over-infections and parasitoses, micro-organism population of skin and/or fur and of enhancing the recovery capacity of the skin and/or fur, preventing, correcting and/or treating cutaneous affections related to troubles with the microflora of the animal skin.

DESCRIPTION OF THE INVENTION

This is achieved by using an active compound selected from the group of a sphingoid base, a sphingoid base derivative or a mixture of two or more of these compounds for manufacturing a cosmetic composition suitable for topical application with animals having an at least partly fur covered skin, for maintaining and/or repairing the keratoseborrheaic condition of the skin and/or fur.

The animal skin differs from the human skin mainly by the presence of a fur being a dense coat of hair, which plays an essential role in the protection of the homeostatic equilibrium. The fur forms an essential element in the thermo-regulation of the animal, towards heat as well as cold, the process of regular moulting assisting this adaptation. Proper functioning of the fur is ensured by the presence of a lipid film on the fur, which originates from sebum secreted by the animal skin. The sebum has been found to intervene in the mechanisms of keratinisation and desquamation of the skin. However, over sebum production accumulates on the skin, the sebum becoming rancid and involving the occurrence of primary sebborheae, i.e. yellowish brown scales. In case of insufficient sebum secretion the skin will in general turn dry, scaly, flaky.

It has now been found that through application of a composition containing a sphingoid base or a derivative thereof, anomalies occurring with sebum secretion by the skin to the fur may be regulated, by which in turn the processes of desquamation and physiological keratinisation of the skin are regulated. Topical application of the active compound of this invention to the animal fur has been found to stimulate de novo-synthesis of ceramides in the stratum corneum. This de-novo synthesis involves an improvement of the keratinisation process and a strengthening of the stratum corneum as well as a proper functioning of the mechanisms of desquamation and physiological keratinisation of the skin. The inventors believe that this may be attributed to the fact that sphingoid bases are lipid compounds, which show an improved interaction with the sebum.

The proper functioning of the mechanisms of desquamation and physiological keratinisation of the skin allows minimising alterations occurring with the microflora residing on the skin and in the fur. This proper functioning in particular allows regulating residential microflora population and controlling population by opportunistic strains, such as *Staphylococcus intermedius* and *Malassezia pachydermatis*, which are the most frequently occurring microorganisms with pet-animals. By controlling the bacterial population of skin and fur, inflammation problems and the associated occurrence of lesions resulting from a malfunctioning of the keratinisation process may be minimised. Simultaneously, growth of pathogenic strains, which is enhanced by the presence of lesions, may be controlled.

In particular, it is believed that the effect of the active compound of this invention can be explained by two synergistic effects. The presence of a dense coat of hair on the animal skin constitutes a focus for the growth of microorganisms, which entails an increased risk to the occurrence of infections. Topical application of the composition of this invention interferes in that due to its anti-microbial properties, the building of an overpopulation of microorganisms on skin and fur may be counteracted. Thus, the ecoflora of the animal fur can be controlled.

Besides this, topical application of the composition of this invention has been found capable of stimulating de-novo synthesis of ceramides, thus enhancing recovery of the animal skin when irritated, inflammated or in case of lesions, and of improving vertical cohesion of skin cells as a result of which skin irritation and the tendency to scratching are counteracted. The minimised risk to inflammations simultaneously allows minimising the risk to overpopulation of microorganisms.

The composition thus shows a dual action, with which both the quality and physical condition and the recovery capacity of the skin and fur may be enhanced and the microorganism population may be controlled. This will in the end result in an improvement of the over-all health of the animal.

Up to now, problems occurring with skin and/or fur of animals had been largely ignored. Nowadays however, owners of animals have become more and more demanding thus stressing the need to provide veterinary compositions capable of preventing and treating those problems. Although the use of sphingo-lipids in compositions for application to the human skin has been reported, there is no indication at all that in the prior art that sphingoid bases, their derivatives or salts would be capable showing one or more of the above described effects with animal fur.

Depending on the nature of the adjuvants, the composition of this invention may be used as a cosmetic composition exerting a preventive effect, for example a hygienic composition that assists in restoring the barrier function of the skin and regulates the microbial population of the skin. The composition of this invention may however also be used from a curative point of view in an advanced dermatologic product, a veterinary medicament or as a complementary product to other medicaments.

The type of sphingoid base used in the composition of this invention is not critical to the invention. The sphingoid base is preferably selected from the group of sphingosin, sphinganin and phytosphingosin, although phytosphingosin is preferred.

The sphingoid base used in the composition of this invention may be obtained from any suitable source, it may for example originate from a natural source, but preferably it is synthesised through a chemical process or fermentation process. To minimise the price of the composition, it is desirable that a sphingoid base is used which is obtainable in reasonable amounts at commercially feasible costs. Chemically synthesised sphingoid base appears to be somewhat expensive, as it is difficult to obtain the desired stereochemical configuration. Animal or vegetal sphingoid base can be obtained from extraction followed by purification of animal and vegetal tissue. Besides the fact that this is an expensive production route, animal sources are believed to be somewhat unsafe due to the regular occurrence of infections that are dangerous to mankind. Therefore, the sphingoid base used in the present invention is preferably obtained from a microbial fermentation process. More preferably it is obtained from a yeast, in particular *Pichia ciferil* as the thus obtainable phytosphingosin has been found to resemble animal skin in the best way. In a preferred embodiment of the invention, phytosphingosin is used as the sphingoid base which is obtained from *Pichia ciferii*-derived tetra-acetyl-phytosphingosin (TAPS), through deacetylation. The deacetylation reaction may be a chemical reaction, for example an alkali catalysed hydrolysis in the presence of KOH, or may be an enzymatic reaction. To obtain a phytosphingosin with a high purity, it may be desirably to subject the phytosphingosin resulting from the hydrolysis reaction to a purification step. Thereto any purification method known to the man skilled in the art may be used.

Suitable examples of sphingoid base derivatives include N-lactyloyl-phytosphingosine, N-salicyloyl-phytosphingosine, N-retinoyl-phytosphingosine, i.e. compounds, which are N-substituted.

Other suitable examples of sphingoid base derivatives include sphingoid base salts. The anion of the salt may be derived from any suitable acid, i.e. those acids, which upon mixing with the sphingoid base in a suitable solid produce a salt with an improved water solubility. The acids which itself are effective when applied to fur or skin are preferred. Preferred salts of the sphingoid base for use in the composition of this invention are the salts obtainable with those acids which upon mixing with the above mentioned sphingoid base in a suitable solvent, produce a salt with an increased water solubility as compared to the water solubility of the sphingoid base as such. The salts of phytosphingosin are preferred for better solubility and better bioavailability.

In one preferred embodiment the acid is a hydrophilic acid capable of delivering the sphingoid base salt to the water phase of the veterinary composition. Suitable hydrophilic acids include α-hydroxy alkanoic acid, a β-hydroxy alkanoic acid, an α,β-dihydroxy alkanoic acid, an alkanedioic acid or a mineral acid. Examples of preferred hydrophilic organic acids are lactic acid, glycolic acid, malic acid, pyruvic acid, succinic acid, fumaric acid, ascorbic acid, gluconic acid and/or pyroglutamic acid. Examples of preferred mineral acids are hydrochloric acid, nitric acid and/or phosphoric acid.

In another preferred embodiment, the acid is a lipophilic organic acid to allow increasing both the efficacy of the lipophilic acid and the sphingoid base in the sphingoid base salt.

In general, the sphingoid base salts will be prepared prior to their inclusion in the composition, as the inclusion in the veterinary composition of the sphingoid base as such and one or more of the above described acids will in general not result in an increased efficacy. A preferred process for preparing the sphingoid base salts of this invention is described in WO 00/53568 which is here incorporated by reference.

The inventor has further found that an effective dose of a composition will usually contain 1-500 mg of the active sphingoid base compound. The posology will usually be adapted to the phenomenon to be treated and the characteristics of the animal, e.g. type of animal, animal weight, age etc. In case of animals with a weight between approximately 5-50 kg such as for example domestic animals, usually two administrations per day will suffice when treating a disorder. For preventive treatment purposes one or a few administrations per week will most often be sufficient. The frequency and dose may however be adapted to the specific type of animal.

Preferred concentrations of the active compound in the dermatological composition of this invention preferably range from 0.001-20 wt. % of the active compound. The preferred concentration will usually be adapted to the type of application envisaged. More preferred concentrations may vary from 0.005-10 wt. %, 0.01 to 5 wt. %, 0.02-2.5 wt. %. Compositions intended for treating disorders will typically contain a higher amount of active compound than compositions intended for preventive use, e.g. normalisation of the flora of the fur and/or skin. Compositions intended for regulating the desquamative condition or controlling overpopulations of micro-organisms or fungicides will most often contain 0.05-5 wt. % of the veterinary composition of this invention.

To allow curing specific or severe distortions, the composition of this invention may contain one or more compounds capable of improving the targeting to the location to be treated or the efficacy or having complementary activity to the active compounds of this invention. Examples of such compounds include (pseudo-) ceramides, preferably skin-identical ceramides, alpha-hydroxy acids for example lactic acid, citric acid, glycolic acid, beta-hydroxy acids for example salicylic acid, and derivatives of the afore mentioned hydroxy-acids, cytokines, anti inflammatory steroids and non-steroids, vitamine A, C, D, E, PP, biotin and B-type vitamins, hormones, benzoyl peroxide, various emollients, ureum, reductants, anti moth agents, antibiotics, anti-fungal agents, disinfectants and any other compounds with complementary activity known to the man skilled in the art.

The composition of this invention may further comprise an amount of one or more suitable adjuvants and/or formulation additives to render the composition suitable for application in the selected mode of administration of the veterinary composition, to assist in delivering the active compound to the required site, if so desired assist in dispersing the active compound over the complete epidermal surface and to allow the active compound to be maintained in an active condition for a period sufficiently long to prevent repetition of the distortion. In particular the compositions of this invention may contain one or more solvents, preferably water, an emollient for example a fat or an oil, or emulsions in which a mixture of water and fat or oil are used as solvent. Other suitable adjuvants include amongst others known to the man skilled in the art, gelling agents, softening agents, emulsifying agents, surfactants, and preservatives.

The surfactant for use with the composition of this invention is preferably selected from the group of ionic surfactants, anionic and/or cationic surfactants, and non-ionic surfactants. However, the use of cationic surfactants is preferred as they provide an enhanced targeting and fixation of the active compound to the site to be treated. Other preferred surfactants include betaines, ethoxylated sorbitan esters for example Tween 80, laureth sulphate or glycol distearate for example Texapon® or Sinnoflor®.

The concentration of the surfactant will mostly vary from 0.01-10 wt. %, preferably from 0.1-5 wt. % or 0.5-2.5 wt. %.

Suitable gelling agents include polyacrylamides for example Carbopol®, acryalte/acrylic acid copolymers for example Aculyn®, acrylamide/acrylamido acid propane sulfite, cellulose derivatives, e.g. hydroxypropylcellulose and Klucel®, vegetal muco-polysaccharides, waxes e.g. bee wax, natural gums e.g. xanthane gum.

Examples of suitable emulsifying agents are those known to the man skilled in the art of veterinary products, for example sorbitan ester polysorbate, sorbitan stearate or laurate, stearic acid derivatives, propylene glycol stearate, polyethylene glycol steareth, a steareth or a ceteareth. In case the composition of this invention is formulated as an emulsion, the emulsion is preferably a submicron emulsion the particle size of which is preferably between 50-200 μm. Such emulsions may be applied in the usual manner, for example by spraying, aerosol.

Suitable softening agents include fatty alcohols or esters, isostearylic alcohol based products, sorbitol-polysaccharides for example Soothex®, Rhamnosoft®.

The cosmetic composition of this invention may be applied in the form of a shampoo, foaming baths, spray, spot on, lotion, gels, emulsion, or other forms of application known to the man skilled in the art may also be used. A spray will mostly be used in curative application, whereas a shampoo mostly will have a cleaning and preventive function and a lotion is especially suitable for cleaning of exsudative lesions and ensures a major antiseptic action without distorting the microflora of the fur.

Although the composition of this invention may contain one or more preservatives, the presence thereof may be omitted without this adversely affecting the stability of the composition. It is thus possible to prepare veterinary dermatologic compositions, which are free of purposely added preservatives. However, if the circumstances so require or favour a suitable preservatives may be incorporated, for example a preservative selected from the group including methyl p-hydroxy-benzoate (methylparaben), propyl p-hydroxy-benzoate (propylparaben), Hinokitiol®.

Application of the composition of this invention to animals with varying kinds of distortions, has evidenced that the active compounds of this invention present properties which have not been disclosed in or could not be expected from scientific or patent publications, nor from any results obtained when applied to the human skin.

In this respect, it has been experimentally evidenced for the first time that phytosphingosin shows anti-microbial activity against specific types of animal staphylocoques. It has been surprisingly found that the multiplication of *Staphylococcus Intermedius* cultures present on animal fur may be partly inhibited by administering 5 ppm of phytosphingosin or its hydrochloric acid salt and completely inhibited by administering 10 ppm of phytosphingosin or its hydrochloric acid salt. The minimum inhibitory concentration in case of *Malassezia pachyadermatis* was 25 ppm. Experiments were carried out using doses of 0, 5, 10, 25, 50 and 100 ppm of phytosphingosin and its hydrochloric acid salt on *Staphylococcus Intermedius* in usual culture environment without solubilising agent.

Preliminary clinical experiments, in-vitro mycological studies have evidenced anti-fungal action of phytosphingosin against *Malassezia pachydermatis*, which is a frequently occurring distortion in the animal race as well as a regulating and corrective action to distorted cutaneous ecoflora of pet animals such as cats and dogs. However the effect is not limited to cats and dogs but extends to other furry animals, such as horses, rabbits, The experiments have shown that the veterinary composition of this invention allows to simultaneously assisting in curing inflammatory phenomena as well as solving primitive or secondary keratinisation problems. These effects are obviated by for example an over-all improvement of the quality of the fur, the smell, pruritus and desquamation.

A comparative study has been carried out to a group of seven dogs which showed a pathological fur: 4 dogs with DAPP, (atopic dermatitis) due to flee bites, one of which is associated with chronic seborrheaic dermatitis, two dogs showed atopi and one dog showed seborrhea. All dogs were treated with the composition of this invention in the form of foam, once a day for a period of 3 days, followed by two applications per week for three weeks.

The results obtained when treating DAPP with a medicament based on an association of the composition of this invention with fipronil (Frontline®) have been compared with the results obtained with a medicament based on an association of fipronil with anti-inflammatory non-steroid. In another study the effect to atopy has been evaluated of a treatment with an antiseptic foaming base in combination with a corticoid (beta-methason) on the one hand and a treatment with the veterinary composition of this invention.

The above-disclosed experiments have evidenced that with the veterinary composition of this invention an important improvement can be obtained of the pruritus, inflammation and desquamation as compared to the known medicaments. When applied to the whole epidermal surface of the animal, the composition of this invention showed prolonged activity, thus allowing to prevent the occurrence of consequential distortions with the animal as well as distortions resulting from stress implied with the animal. Besides this, the veterinary compositions of this invention appear to show improved drying properties, easy to apply, provide excellent cleaning properties and excellent after-treatment properties.

The above-described experiments have shown that the veterinary composition of this invention can be successfully used in hygienic products as well as in veterinary medicine, in particular with cats and dogs, for treating all inflammatory pathologies related to stress, parasitoses, dermatoses, atopic dermatitis, superinfection folliculites, modifications of the flora, contact eczema.

Shampoo or foaming bases containing the veterinary composition of this invention proved to be particularly suitable for preventing and correcting cutaneous problems associated with a proliferation of *Malassezia pachydermatis* or *Staphylococcus intermedius*. Emulsions, alcoholic lotions or sub-micronic emulsions, sprays, spot-on formulations are suitable for preventing fungal affections. When treating chronical superficial folliculites of a dog, when preventing of fungal affections preferably use is made of a gel or a micellar lotion, which is adapted to cleaning exsudative lesions. Dermatoses or superinfections involved by *Staphylococcus intermedius* can be successfully treated with a cream.

The invention is further illustrated in the following examples.

Example 1

A sub-micron lotion for spraying was prepared with the following composition (amounts given in parts by weight):

| | |
|---|---|
| phytosphingosin | 0.20 |
| isodecyl isononanoate | 15.00 |
| octyldodecanole | 10.00 |
| diethylhexylcyclohexane | 5.00 |
| squalane | 5.00 |
| butylene glycol | 3.00 |
| Quaternium 82 | 2.00 |
| cetyl dimethicon copolyol | 1.50 |
| isostearyl alcohol | 0.50 |
| chlorphenesine | 0.20 |
| conservatives | 0.60 |
| water | up to 100 |

Example 2

A gel for topical application was prepared with the following composition (given in parts by weight)

| | |
|---|---|
| Base gel | |
| hydroxypropyl cellulose | 3.30 |
| ethoxydiglycol | 13.33 |
| ethanol 96° | 83.34 |
| Composition of the gel: | |
| base gel | 45.00 |
| ethanol 96° | 27.30 |
| cyclomethicone | 11.50 |
| alkylene lactate C12-C13 | 13.50 |
| isostearyl alcohol (Soothex ®) | 2.50 |
| phytosphingosin | 0.20 |

Example 3

An emulsion for a foaming bases was prepared as known to the man skilled in the art, having the following composition (amounts given in parts by weight):

| | |
|---|---|
| Phytosphingosin hydrochloric acid | 0.25 |
| surfactant (Texapon ®) | 64.00 |
| cyclomethicone | 2.50 |
| acrylate copolymer | 6.50 |
| triethanolamine | 1.10 |
| ethanol 96° | 1.00 |
| softening agent | 4.50 |
| preservative | 0.20 |
| water | up to 100 |

Example 4

Five different shampoos were prepared based on the following ingredients:

|  | A | B | C | D | E |
|---|---|---|---|---|---|
| Demineralised water | 56.75 | 40 | 44 | 38 | 38 |
| UCARE POLYMER JR 400 | 0.5 | 0.5 | 0.5 | 0.5 | 0.5 |
| Phytosphingosine.HCl | 0.1 | 0.1 | 0.1 | 0.10 | — |
| Detergent TEXAPON | 10 | 10 | 10 | 15 | 15 |
| Protective agent Fomblin HC04 | 0.2 | 0.2 | 0.2 | 0.2 | 0.2 |
| Perfume | 0.2 | 0.2 | 0.2 | 0.2 | 0.2 |
| PHENOXYETHANOL | 0.50 | 0.5 | 0.5 | 0.5 | — |
| ACULYN | 4 | 4 | 4 | 4 | 4 |
| Triethylamine | 0.8 | 1.21 | 1.25 | 1.12 | 0.9 |

Example 5

42 dogs of various ages and races suffering from primary kerato-seborrhaeic affections were treated with the shampoos of example 4 for two months, once a week.

A first group of dogs was treated with shampoo A. Shampoo A showed insufficient foaming and induced unsatisfactory brilliance to the fur. Regulation of keratinisation process and control of odour was found insufficient. No sign of irritation A second, third and fourth group of dogs were treated respectively with shampoo B, C and D showed good control of odour, D providing the optimum performance with respect to regulation of keratinisation process and control of odour.

Shampoo D contained phytosphingosin salt and a cationic surfactant.

A fifth group was treated with shampoo E, which showed no activity.

Example 6

20 dogs of various ages and races suffering from acquired and primary kerato-seborrhaeic troubles were treated with the shampoo D of example 4.

Application of the shampoo once a week during four weeks allowed controlling the odour of all dogs. A good improvement of pruritis was observed with 14 dogs, a rapid action with improved fur of all dogs. Infections of Malassezia and chronical secondary folliculites could be cured with 5 dogs out of 7. Chronical secondary follicles could be controlled with 4 dogs out of 6, affections caused by exo-prasitoces (lice) could be ameliorated with 5 dogs out of 8.

Example 7

A spray was prepared using the following ingredients:

| Ingredients | wt. % |
|---|---|
| Demineralised water | up to 100 |
| Potassium sorbate | 0.2 |
|  | 4.0 |
| Cetiol A | 10 |
| Phytosphingosine | 0.20 |
| Perfume | 0.15 |
| Softening agent SOOTHEX | 0.50 |

-continued

| Ingredients | wt. % |
|---|---|
| Glycerine | 3 |
| 20% citric acid | 0.935 |

10 dogs showing seborrheaic dermatitis were treated with a hydro alcoholic lotion, which contained no phytosphingosin. No amelioration of the affection was observed. Subsequent treatment, once a week for four weeks with the lotion with the above given composition, the treatment being continued where necessary, revealed a rapid action and that the odour could be controlled with all dogs. Over population of the micro-organisms could be controlled in 9 of 10 cases.

Example 8

6 dogs which showed no amelioration when treated with the shampoo of example 4, were treated once a week with the spray of example 7, which contained twice the amount of phytosphingosin as compared to the shampoo.

A quick amelioration of the affection was established, odour ameliorated quickly and population of micro-organisms could be controlled.

Similar effects were observed when treating 4 other dogs with the spray and the shampoo, once a week for a period of 4 weeks.

Example 9

The effect of the spray of example 7 was tested with 10 dogs, using daily application during 4 weeks.

Two dogs showed pyodermites, which completely disappeared, one dog showed pyo traumatic dermatitis, which completely disappeared. Three dogs showed ear infections, which completely disappeared, two dogs showed dermatoses of the invullen, which completely disappeared.

Example 10

A micellar lotion was prepared using the following ingredients (wt. %):

| Demineralised water | up to 100 |
|---|---|
| Denaturated alcohol 96° | 5 |
| Eau demineralisee | 10 |
| Phytosphingosin HCl | 0.02 |
| Polysorbate (TWEEN 80) | 5 |
|  | 2 |
|  | 2 |
|  | 2 |
| potassium sorbate | 0.10 |
| Phenoxyethanol | 0.30 |
| Propylene glycol | 3 |
|  | 0.40 |
| citric acid 10% solution | 0.55 | pH was adjusted to 4.75

The lotion was tested for its performance with 30 dogs on its cleaning properties in creases, connection zones (periocular zones, dirty and pathological ears). The lotion showed good cleaning properties and excellent tolerance, without inducing the usual allergic reactions which appear when using antiseptic agents. An effective anti-microbial activity was observed in 26 cases out of 30.

The composition of this invention may be used as a cosmetic or pharmaceutical composition in veterinary products and allows reestablishing of the animal ecoflora, preventing, correcting and treating cutaneous phenomena with animals which are related to problems occurring in the ecoflora, for example microbial or fungal sur-population, or problems occurring in the pathologic development of a specific microorganism. The composition of this invention is capable of positively interfering in keratinisation problems occurring with the animal, it provides anti-microbial, anti-fungal, in particular anti-yeast and anti-inflammatory activity, in particular allows preventing and/or correcting inflammations related to specific parasitoses and dermatoses for example eczema, or originating from varying aggressions such as stress. The intensive scratching by the animal associated with such condition, which otherwise ensues a distorted ecoflora, lesions occurring in the skin and fur, inflammatory reactions and aggravated keratinisation problems, being minimised. The composition of this invention is suitable for use in the preparation of a veterinary medicament suitable for treating inflammations which may result from varying aggressions, for example from stress or be related to specific parasitoses and dermatoses.

The compositions of this invention may be used in a more general manner to control kerato seborrheaic condition of skin and fur, to regulate the desquamative status and to control microbial and fungal overpopulations of skin and fur. The ability of a composition containing a sphingoid base of regulating a mal functioning cutaneous barrier involves an improved resistance to immunologic reactions, decreased risk to microbial and fungal sensitivity, decreased bacterial proliferation, pilar anomalies and inflammatory responses.

The invention claimed is:

1. A method of treating conditions of the skin and fur of a veterinary animal having an at least partly fur covered skin in need thereof comprising administering by topical application to the fur of the animal a composition comprised of an active compound selected from a sphingoid base, a sphingoid base derivative or a mixture of two or more of said compounds, wherein the condition comprises infection associated with the presence of *Staphylococcus Intermedius* and/or *Malassezia Pachydermatis*.

2. The method of claim 1, wherein the active compound is selected from the group of sphingosin, sphinganin, phytosphingosin or a mixture of two or more of these compounds.

3. The method of claim 1, wherein the sphingoid base derivative is a salt of phytosphingosin selected from the group of a α-hydroxy alkanoic acid salt, a β-hydroxy alkanoic acid salt, an α,β-dihydroxy alkanoid acid salt, an alkanedioic acid salt, a mineral acid salt or a lipophilic organic acid salt.

4. The method of claim 1, wherein the sphingoid base derivative is a lactic acid, glycolic acid, malic acid, pyruvic acid, succinic acid, fumaric acid, ascorbic acid, gluconic acid, pyroglutamic acid, a hydrochloric acid, nitric acid and/or phosphoric acid salt of phytosphingosin.

5. The method of claim 1, wherein the sphingoid base derivative is a N-substituted derivative of phytosphingosin.

6. The method of claim 5, wherein the sphingoid base derivative is selected from the group of N-lactyloyl-phytosphingosine, N-salicyloyl-phytosphingosine or N-retinoyl-phytosphingosine.

7. The method of claim 1, wherein the composition contains a cationic surfactant.

8. The method of claim 1, wherein the composition contains 0.001-20 wt. % of the active compound.

9. The method of claim 1, wherein the composition contains 0.005-10 wt. % of the active compound.

10. The method of claim 1, wherein the composition contains 0.01-5 wt. % of the active compound.

11. The method of claim 1, wherein the composition further comprises an additive capable of exhibiting a complementary activity, the additive being selected from the group of alphahydroxy acids, lactic acid, citric acid, glycolic acid, beta-hydroxy acids, salicylic acid and derivatives of the aforementioned hydroxy-acids, cytokines, anti-inflammatory steroids and non-steroids, vitamins A, C, D, E, PP, biotine and B-type vitamins, hormones, benzoyl peroxide, various emollients, ureum, reductants, anti-moth agents, antibiotics, anti-fungal agents or disinfectants.

12. The method of claim 1, wherein the composition is in the form of a shampoo, foaming base, spray, spot on, lotion, gel or emulsion of the active compound.

13. The method of claim 1, wherein a single dose of the composition contains 1-500 mg of the active compound.

14. The method of claim 1, wherein the composition takes the form of an emulsion with a mean particle size of between 50-200 nm.

15. The method of claim 1, wherein the topical application corrects cutaneous affections related to problems with the microflora of the animal skin.

16. The method of claim 1, wherein the animal skin is covered by a dense coat of fur with a lipid film on the fur.

17. The method of claim 1, wherein the animal is a furry animal.

18. The method of claim 17, wherein the animal is a cat, dog, horse, or rabbit.

19. The method of claim 18, wherein the animal is a cat or dog.

* * * * *